United States Patent
Kinoshiro et al.

(10) Patent No.: US 10,287,644 B2
(45) Date of Patent: *May 14, 2019

(54) MOLTEN STEEL DESULFURIZATION METHOD, MOLTEN STEEL SECONDARY REFINING METHOD, AND MOLTEN STEEL MANUFACTURING METHOD

(75) Inventors: Satoshi Kinoshiro, Kawasaki (JP); Toshiyuki Ito, Kawasaki (JP); Ryo Kawabata, Oota (JP); Toshiro Ishige, Yokohama (JP); Kyoko Fujimoto, Chiba (JP); Masao Inose, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 662 days.

This patent is subject to a terminal disclaimer.

(21) Appl. No.: 14/123,688

(22) PCT Filed: Aug. 8, 2012

(86) PCT No.: PCT/JP2012/070204
§ 371 (c)(1),
(2), (4) Date: Dec. 3, 2013

(87) PCT Pub. No.: WO2013/024766
PCT Pub. Date: Feb. 21, 2013

(65) Prior Publication Data
US 2014/0096643 A1 Apr. 10, 2014

(30) Foreign Application Priority Data

Aug. 12, 2011 (JP) ................................. 2011-176633
Aug. 12, 2011 (JP) ................................. 2011-176635
Aug. 1, 2012 (JP) ................................. 2012-171212

(51) Int. Cl.
*C21C 1/02* (2006.01)
*C21C 7/00* (2006.01)
(Continued)

(52) U.S. Cl.
CPC .............. *C21C 7/0645* (2013.01); *C21C 1/02* (2013.01); *C21C 7/0006* (2013.01);
(Continued)

(58) Field of Classification Search
None
See application file for complete search history.

(56) References Cited

U.S. PATENT DOCUMENTS 3,363,427 A * 1/1968 Smith ........................ F25J 3/08
62/656
4,360,381 A 11/1982 Tarutani et al.
(Continued)

FOREIGN PATENT DOCUMENTS

JP    A-59-083054    5/1984
JP    S61-191956 A   8/1986
(Continued)

OTHER PUBLICATIONS

JP 2009-144221 machine translation provided with Dec. 3, 2013 IDS.*

(Continued)

*Primary Examiner* — Keith Walker
*Assistant Examiner* — Stephani Hill
(74) *Attorney, Agent, or Firm* — Oliff PLC

(57) ABSTRACT

A method for desulfurizing molten steel comprising taking a sample out from molten steel after tapping from a converter or during secondary refining and analyzing the sample rapidly with high accuracy by a method comprising a high frequency induction heating step wherein the sample is combusted and oxidized under the high frequency induction heating in an oxygen atmosphere having an oxygen purity of 99.5 vol % or more to convert S in the sample into $SO_2$ and an analyzing step wherein $SO_2$-containing gas produced in the high frequency induction heating step is analyzed (Continued)

through an ultraviolet fluorescence method to quantify S concentration of the sample.

8 Claims, 3 Drawing Sheets

(51) Int. Cl.
    *C21C 7/06*     (2006.01)
    *C21C 7/10*     (2006.01)
    *C21C 7/064*     (2006.01)
    *G01N 21/64*     (2006.01)
    *G01N 33/00*     (2006.01)
    *F27D 19/00*     (2006.01)
    *F27D 21/00*     (2006.01)

(52) U.S. Cl.
    CPC .......... *C21C 7/0037* (2013.01); *C21C 7/0075* (2013.01); *C21C 7/0087* (2013.01); *C21C 7/06* (2013.01); *C21C 7/064* (2013.01); *C21C 7/10* (2013.01); *F27D 19/00* (2013.01); *F27D 21/00* (2013.01); *G01N 21/64* (2013.01); *G01N 21/645* (2013.01); *G01N 33/0042* (2013.01); *C21C 2007/0093* (2013.01); *C21C 2300/08* (2013.01); *Y02A 50/248* (2018.01)

(56) References Cited

U.S. PATENT DOCUMENTS

| | | | |
|---|---|---|---|
| 4,582,686 A | 4/1986 | Tsuji | |
| 4,944,798 A | 7/1990 | Ototani | |
| 4,994,398 A * | 2/1991 | Yamada | C22C 1/045 419/66 |
| 5,149,364 A | 9/1992 | Craig et al. | |
| 5,152,963 A * | 10/1992 | Wreyford | G01N 21/64 422/80 |
| 5,424,217 A | 6/1995 | Benner et al. | |
| 7,244,395 B2 * | 7/2007 | Olstowski | G01N 21/643 422/80 |
| 2006/0250614 A1 | 11/2006 | Plessers et al. | |
| 2006/0272447 A1* | 12/2006 | Peaslee | B22D 11/116 75/10.62 |
| 2013/0196445 A1* | 8/2013 | Kinoshiro | G01N 21/643 436/123 |
| 2017/0009311 A1* | 1/2017 | Adachi | C21C 1/025 |

FOREIGN PATENT DOCUMENTS

| | | | | |
|---|---|---|---|---|
| JP | H03010014 A * | 1/1991 | ............... | C21C 7/00 |
| JP | H08-94609 A | 4/1996 | | |
| JP | A-11-006009 | 1/1999 | | |
| JP | A-11-051924 | 2/1999 | | |
| JP | 2000065699 A * | 3/2000 | ............... | G01N 1/22 |
| JP | A-2000-065699 | 3/2000 | | |
| JP | 2001-323314 A | 11/2001 | | |
| JP | A-2003-155516 | 5/2003 | | |
| JP | A-2003-342631 | 12/2003 | | |
| JP | 2004-138466 A | 5/2004 | | |
| JP | A-2005-179762 | 7/2005 | | |
| JP | 2005-290434 A | 10/2005 | | |
| JP | 2006-322863 A | 11/2006 | | |
| JP | 2007051350 A * | 3/2007 | | |
| JP | A-2007-051350 | 3/2007 | | |
| JP | A-2008-063647 | 3/2008 | | |
| JP | A-2008-169407 | 7/2008 | | |
| JP | 2009144221 A * | 7/2009 | ............... | C21C 7/00 |
| JP | A-2009-144221 | 7/2009 | | |
| JP | 2009191300 A | 8/2009 | | |
| JP | A-2009-191289 | 8/2009 | | |
| JP | 2010163697 A | 7/2010 | | |
| JP | 2011-080143 A | 4/2011 | | |
| JP | WO 2011102137 A1 * | 8/2011 | ........... | G01N 21/643 |
| JP | A-2011-169753 | 9/2011 | | |
| JP | 2011-237204 A | 11/2011 | | |
| KR | 20050007494 A | 1/2005 | | |

OTHER PUBLICATIONS

JP 2000-065699 machine translation provided with Dec. 3, 2013 IDS.*
JP 2007-051350 espacenet translation.*
G. A. Tipler. "Rapid determination of carbon in steel by infrared gas analysis." Analyst, vol. 88, Apr. 1963. pp. 272-279.*
R. Burnett. "Induction Heating." http://www.richieburnett.co.uk/indheat.html. Accessed Jul. 26, 2016.*
WO 2011/102137 machine translation.*
"Secondary Refining". Chapter 2 Smelting, Refining and Continuous Casting. 2003. Supplied by applicant on Nov. 18, 2016.*
JP H03-010014 machine translation (Year: 1991).*
"An Introduction to Fluorescence Spectroscopy" PerkinElemer (2000) (Year: 2000).*
Model T100H UV Fluorescence SO2 Analyzer. Mar. 25, 2011. (Year: 2011).*
Sutherland. 1 Basic Principles. Filters and Filtration Handbook (5th Edition). 2008. p. 1-40. With citations in the form of page: paragraph (Year: 2008).*
ASTM D7183-07 (Apr. 2007.) (Year: 2007).*
Sep. 1, 2015 Extended Search Report issued in European Patent Application No. 12823682.5.
Tetsu-to-Hagane, As to desulfurization method using agitationblade, 1972, vol. 58, No. 4, p. 34.
Kurokawa et al., The Development in Hot Metal Desulphurization Process, Sumitomo Metal Technical Reports, 1993, vol. 45, No. 3, pp. 52-58.
Tesu-to-Hagane, As to desulfurization of hot metal by means of quicklime, 1978, vol. 64, No. 2, pp. A21-A24.
Dec. 24, 2014 Office Action issued in U.S. Appl. No. 14/119,692.
Sep. 11, 2012 Search Report issued in International Application No. PCT/JP2012/070202.
May 17, 2015 Office Action issued in Korean Patent Application No. 2014-7002387.
International Preliminary Report on Patentability issued in International Application No. PCT/JP2012/070204 dated Feb. 18, 2014.
International Search Report issued in International Application No. PCT/JP2012/070204 dated Oct. 30, 2012.
Dec. 2, 2015 Office Action issued in Japanese Patent Application No. 2012171212.
Apr. 17, 2014 Office Action issued in U.S. Appl. No. 13/579,989.
Sep. 25, 2013 Office Action issued in U.S. Appl. No. 13/579,989.
Syty Augusta "Determination of Sulfur Dioxide by Ultraviolet Absorption Spectrometry" Analytical Chemistry, vol. 45, No. 9, Aug. 1973, p. 1744-1747.

* cited by examiner

【Fig.1】
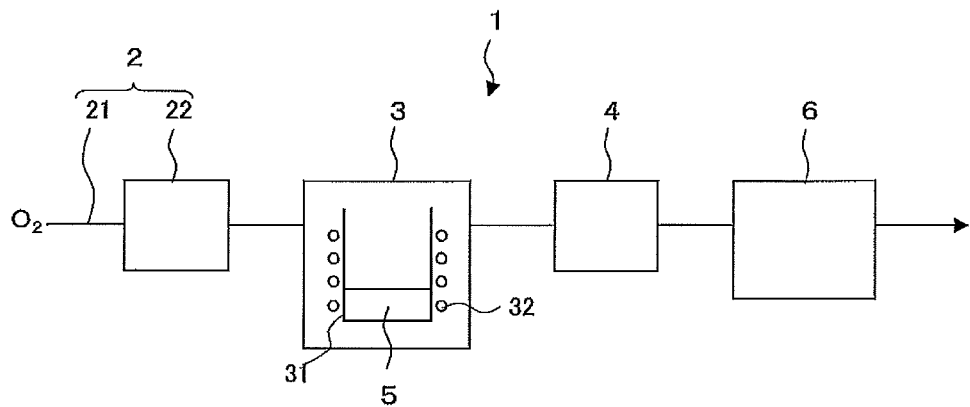
【Fig.2】
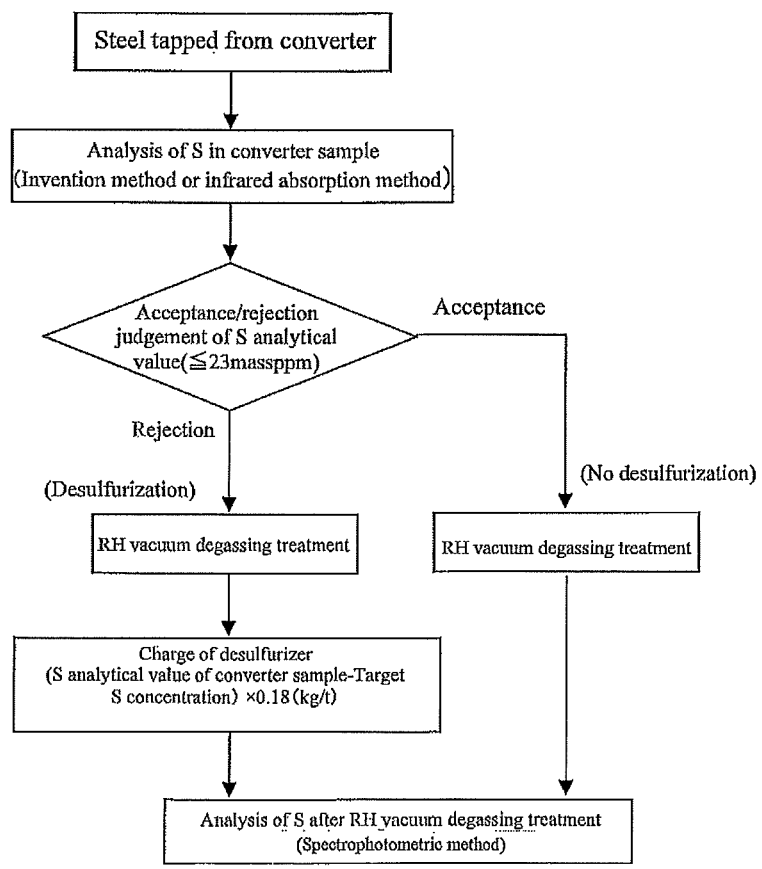

【Fig.3】
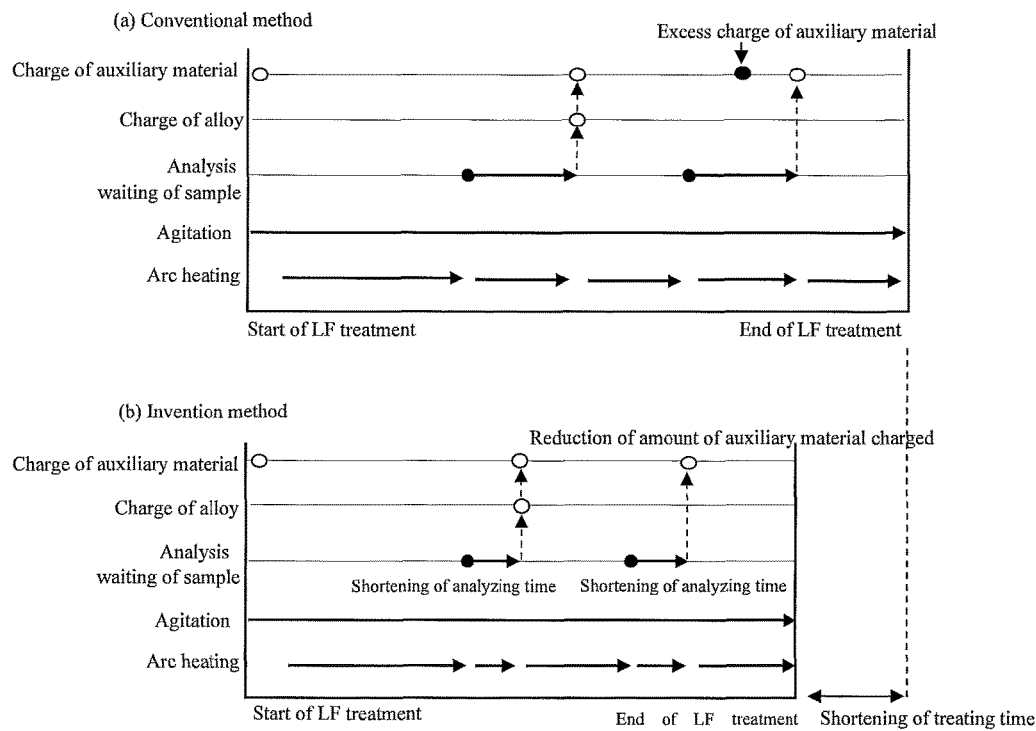
【Fig.4】
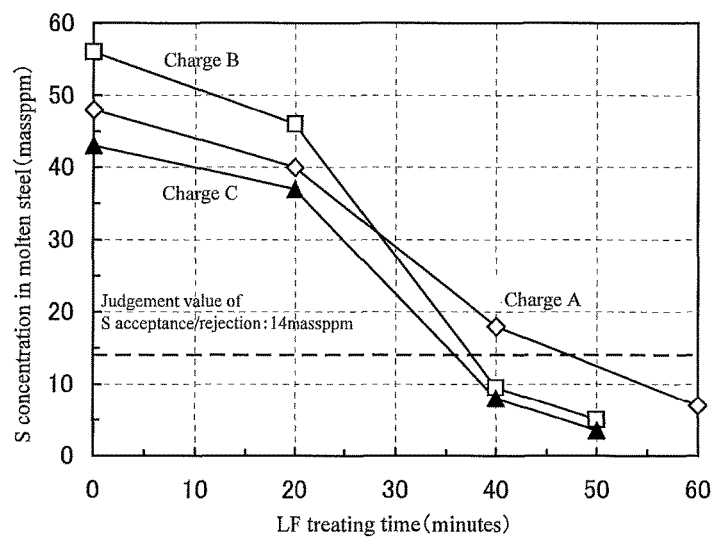

[Fig.5]
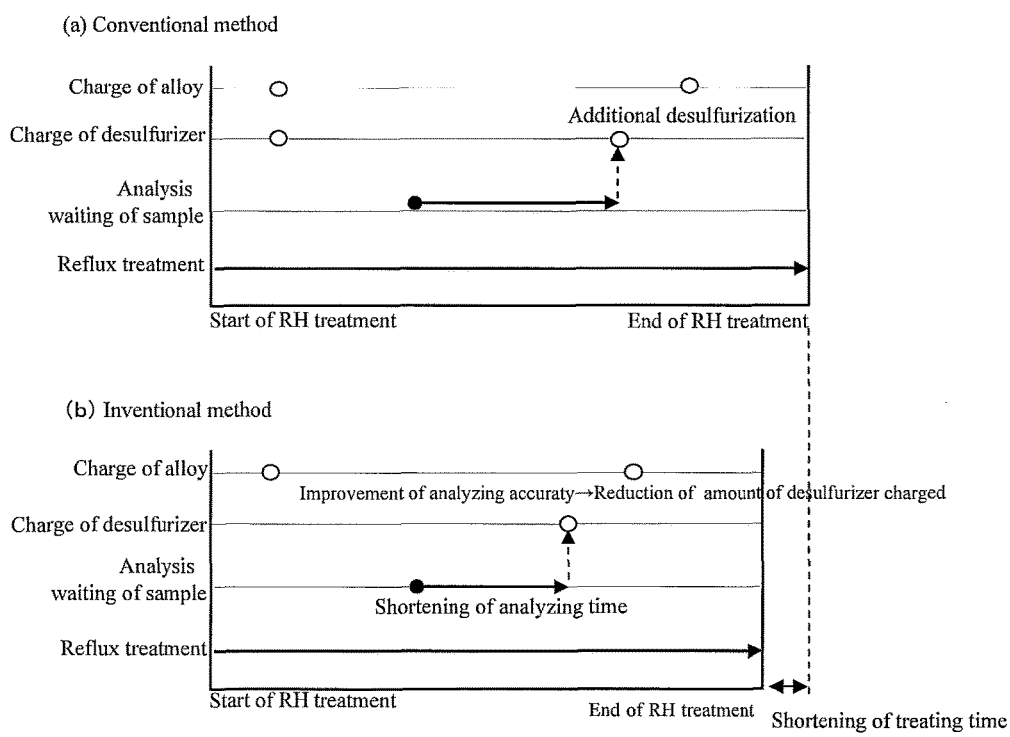

MOLTEN STEEL DESULFURIZATION METHOD, MOLTEN STEEL SECONDARY REFINING METHOD, AND MOLTEN STEEL MANUFACTURING METHOD

TECHNICAL FIELD

The first aspect of this invention relates to a method for desulfurizing molten steel and a method of manufacturing molten steel, and more particularly to a method for desulfurizing molten steel which is capable of controlling S concentration after desulfurization in a high accuracy by rapidly and accurately analyzing S concentration in molten steel after the tapping from a converter, and a method of manufacturing molten steel by using such a desulfurization method.

The second aspect of this invention relates to a method for secondarily refining molten steel and a method of manufacturing molten steel, and more particularly to a method for secondarily refining molten steel which is capable of shortening a time required for desulfurization and reducing an amount of a desulfurizer used by rapidly and accurately analyzing S concentration in molten steel during the secondary refining, and a method of manufacturing molten steel by using such a method.

RELATED ART

Recently, the demand for improving the quality of steel products is increasing and hence it is an important issue to reduce S concentration in steel. Since S contained in the steel products is derived almost from iron ore or coke, a great amount of S is contained in hot metal tapped from a blast furnace. Now, desulfurization for reducing S in hot metal or molten steel is carried out at a step after the tapping from the blast furnace.

In general, the process conducting the desulfurization is roughly classified into a process for subjecting hot metal to a preliminary treatment and a secondary refining process. Even in these processes is mainly used a desulfurizer containing lime (CaO) as an essential ingredient. In this case, the desulfurization reaction progresses based on the following reaction formula:

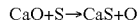

In the above reaction formula, activity coefficient of S becomes larger as carbon concentration in steel becomes higher, so that it is efficient to conduct the desulfurization at a hot metal stage containing a great amount of carbon. To this end, after the desulfurization is conducted to a certain level at a stage of preliminarily treating hot metal, it is common to again conduct the desulfurization at a secondary refining process from the converter depending on S level required in a final product.

As a value of S concentration in steel products is used a value obtained by analyzing a sample taken out from molten steel just before casting (hereinafter referred to as "ladle sample"), so that it is general to preliminarily analyze and confirm S concentration of a sample taken out after final adjustment of S prior to the casting in order that the S concentration of the ladle sample does not depart from a standard value (acceptance/rejection criterion) or an upper limit of a target concentration.

In a low-sulfur steel having such a level that a target S concentration is not more than 0.002 mass % (acceptance is less than 25 massppm) or not more than 0.003 mass % (acceptance is less than 35 massppm) or a plain steel having S concentration accepted to more than the above value, it is frequent that S is reduced to not more than the upper limit of the target concentration at a stage of preliminarily treating hot metal and the desulfurization is not conducted at the secondary refining. This is due to the fact that the desulfurization in the secondary refining brings about the increase of power cost for heating molten steel, cost of auxiliary materials such as desulfurizer and the like, and refractory cost associated with erosion of the refractory and hence production cost rises as compared with the preliminary treatment of hot metal.

In case of the low-sulfur steel and plain steel not conducting the desulfurization in the secondary refining, a sample taken out during the tapping from the converter (hereinafter referred to as "converter sample") is generally a sample for preliminary confirmation of S concentration. If the converter sample is the failure of the S concentration, the secondary refining is added to conduct the desulfurization. However, the addition of the secondary refining not only increases the production cost as mentioned above, but also causes disturbance of production steps. For example, if it is intended to desulfurize a charge being out of the S concentration in the secondary refining, the production steps up to continuous casting step are disturbed, which is a cause of obstructing continuous continuous casting of the continuous casting in some cases.

Lately, desulfurizing capacity of a converter slag lowers resulting from a fact that fluoric as a fluorine-containing material cannot be used as a flux in decarbonization refining at the converter (slag forming agent) from a viewpoint of environmental conservation. From the requirement of reducing amount of $CO_2$ generated, iron scrap is used as a raw steel material in the converter and also as the hot metal are partly used not only a hot metal from a blast furnace but also a hot metal obtained from a scrap dissolving furnace of a shaft furnace type. However, the hot metal from the scrap dissolving furnace is relatively high in the S concentration, so that it is difficult to make the S concentration after the preliminary treatment of hot metal to not more than 0.003 mass %. Due to these facts, a ratio that the S concentration of the low-sulfur steel or plain steel departs from the upper limit of the target concentration becomes higher, and hence a ratio of conducting the desulfurization in the secondary refining becomes high even in the low-sulfur steel or plain steel.

In case of an extremely low-sulfur steel wherein a target S concentration is not more than several tens massppm (for example, a target value is not more than 0.001 mass % and an acceptance value is not more than 14 massppm), molten steel after the tapping from the converter is common to be further subjected to desulfurization in the secondary refining. As the desulfurization method is a general a method wherein molten steel is added with a great amount of a desulfurizer and the molten steel is stirred while heating with a ladle refining equipment called as LF (Ladle Furnace) capable of conducting arc heating and slag refining (for example, see Patent Documents 1~4), a method wherein a Ruhrstahl-Heraeus (RH) vacuum degassing apparatus is used and a desulfurizer is projected or charged by injection into molten steel inside the vacuum degassing apparatus (for example, see Patent Documents 5~8) and so on. Especially, LF is suitable for melting the extremely low-sulfur steel.

Moreover, desulfurizing conditions in the production of the extremely low-sulfur steel by desulfurization in the secondary refining, for example, amount of the desulfurizer charged, treating time and the like are determined based on the amount of molten steel, and final S analytical value before the secondary refining. The final S analytical value is the S analytical value of converter sample. As another example of the desulfurizing conditions is an amount of auxiliary material (lime, $Al_2O_3$, $SiO_2$, CaF and the like) charged for obtaining a slag composition suitable for the desulfurization.

In the second aspect of the invention, when multiple charging of the desulfurizer is conducted in the secondary refining, the S analytical value after the desulfurization just before the given charging is considered to be a final S analytical value instead of the final S analytical value before the secondary refining.

In the low-sulfur steel or plain steel conducting the desulfurization only by the preliminary treatment of hot metal, the converter sample is a sample for preliminary confirmation as previously mentioned. In this case, there is no problem when the S analytical value of the converter sample is considerably lower than the upper limit of the target S concentration, but there is a problem when it is near to the upper limit. Because an error is at least present even in any analyzing methods. In the analysis of the ladle sample, therefore, the analytical accuracy is assured by conducting a plurality of measurements in order to reduce the error so as to approach to a true value. In case of the converter sample, however, it is difficult to conduct the plurality of measurements because there is no room in the time.

Even if the S analytical value of the converter sample is below the target upper limit (acceptance), the S analytical value of the ladle sample may exceed the target upper limit (rejection) resulting from the analytical error. Inversely, even if the S analytical value of the converter sample is rejection, it cannot be said that the acceptable possibility is actually zero. Even if it is acceptable, the desulfurization is excessively conducted in the secondary refining, which leads to the increase of the production cost not visible on the surface. In general, the S concentration of the converter sample is frequently near to the target upper limit or near to the value of acceptance/rejection criterion, and the good and bad analytical accuracy becomes potential problem.

Similarly, the operational conditions (desulfurizing conditions) are determined even in the secondary refining based on the S analytical value of the converter sample or the sample taken out in the secondary refining. Even in this case, however, there are problems in the increase of the production cost or decrease of the productivity due to the excessive charging of the desulfurizer for avoiding the failure of the S concentration, prolongation of the treating time and the like. The above avoidance is based on the supposition of the error of the analytical value likewise the low-sulfur steel. Especially, since the S concentration is low in the secondary refining, the error is relatively large. And also, the secondary refining is a final desulfurization step, so that it is actual to excessively cope with the failure of the S concentration.

As a technique for avoiding the failure of the S concentration are disclosed a number of techniques for increasing a basicity of a slag in the refining to enhance the desulfurization capacity (for example, see Patent Document 6). However, the S concentration in steel cannot be confirmed if the analysis is not actually conducted, and also the failure of the S concentration cannot be prevented if there is a problem in the analytical accuracy itself.

As a method of analyzing the S concentration in steel are widely used "Method for spark discharge atomic emission spectrometric analysis" defined in JIS G1253(2002) (hereinafter also abbreviated as "emission spectrometric method"), "Infrared absorption method after combustion in an induction furnace" defined in JIS G1215-4(2010) (hereinafter also abbreviated as "infrared absorption method"), "Methylene blue spectrophotometric method after separation of hydrosulfide" defined in JIS G1215-3(2010) (hereinafter also abbreviated as "spectrophotometric method") and so on.

PRIOR ART DOCUMENTS

Patent Documents

Patent Document 1: JP-A-2003-155516
Patent Document 2: JP-A-2005-179762
Patent Document 3: JP-A-2007-051350
Patent Document 4: JP-A-2009-191289
Patent Document 5: JP-A-H11-006009
Patent Document 6: JP-A-2003-342631
Patent Document 7: JP-A-2008-063647
Patent Document 8: JP-A-2008-169407

SUMMARY OF THE INVENTION

Task to be Solved by the Invention

Among the above analytical methods, the spectrophotometric method is a so-called wet chemical analysis and is high in the analytical accuracy, but a long time such as several hours is usually taken in the measurement. Therefore, this method is not daily used in the analysis of the S concentration at steel-making step, while the two methods capable of analyzing relatively rapidly such as the emission spectrometric method and infrared absorption method are mainly used. In the emission spectrometric method, however, surface nature such as surface roughness or the like on an analyzing surface exerts on the analytical value, so that a smooth surface having a diameter of about 30 mm is required as an analyzing surface, and a polishing time is required, and hence there is a problem that a time is taken until an analytical result on the S concentration is obtained (usually about 15 minutes). Further, a time is taken until molten steel is taken out and poured into a mold for an analytical sample and cooled and a sample is taken out therefrom.

Also, there is a tendency that the emission spectrometric method is poor in the analytical accuracy as compared with the infrared absorption method. To this end, when the S concentration is particularly necessary to be accurately analyzed in the low-sulfur steel or extremely low-sulfur steel, the infrared absorption method is frequently used. Even in the infrared absorption method, however, as shown in Table 7 of JIS G1215-4, an error of ±2 massppm in the extremely low-sulfur steel having an S concentration level of 5~10 massppm and an error of ±5 massppm in the low-sulfur steel having a level of 20~30 massppm are accepted, so that this method has never sufficient analytical accuracy on the extremely low-sulfur steel or low-sulfur steel.

As a method of solving the above measuring error in the infrared absorption method are developed a method of repeating the measurement several times to calculate an average value, and a technique wherein $SO_2$ is collected in an adsorption/condensation column (trap) and then the concentrated $SO_2$ is again released by a slight amount of helium gas to conduct analysis to thereby realize a high accuracy. In these techniques, however, the measurement of the sample is conducted several times or the adsorption/condensation step is added, so that the analysis takes a long time, and there is a problem that it is difficult to apply the techniques to the analysis of S concentration at the steel-making step. In the desulfurization of molten steel at the steel-making step, therefore, there are problems such as failure of S concentration, increase of production cost and so on. Furthermore, excessive desulfurization apprehending about the failure of S concentration was carried out in the secondary refining of molten steel.

The invention is made in view of the above problems retaining in the conventional techniques.

That is, it is an object of the first aspect of the invention to propose a method for desulfurizing molten steel which is capable of controlling S concentration of steel in a high accuracy by rapidly and accurately analyzing S concentration of a sample taken out from molten steel after the tapping from a converter, and a method of manufacturing molten steel by using such a desulfurization method.

Also, it is an object of the second aspect of the invention to propose a method for secondarily refining molten steel which is capable of shortening desulfurization time in secondary refining and also reducing an amount of a desulfurizer or the like used by rapidly and accurately analyzing S concentration of a sample taken out during the secondary refining, and a method of manufacturing molten steel by using such a method.

The reason setting the above objects is due to the fact that when the S concentration can be analyzed rapidly and accurately, the analytical results of S concentration in the converter sample or during the secondary refining are reflected in the subsequent desulfurization refining, whereby not only S concentration in molten steel can be controlled accurately to improve on-target ratio of S concentration but also the excessive addition of the desulfurizer and the prolongation of the treating time become needless. Furthermore, fruitless treating time in the secondary refining can be reduced by accurately grasping the S concentration in molten steel, and hence the productivity can be increased.

Solution for Task

The inventors have made various studies on a method for rapidly and accurately analyzing S concentration in molten steel after the tapping from a converter for solving the above tasks. As a result, it has been found out that the above task can be solved by combusting and oxidizing a sample taken out from molten steel after the tapping from a converter under a high frequency induction heating in a pure oxygen atmosphere to convert all S included in the sample into $SO_2$ for a short time and analyzing a concentration of $SO_2$ through an ultraviolet fluorescence method, and the first aspect of the invention has been accomplished.

That is, the first aspect of the invention is a method for desulfurizing molten steel by taking out a sample from molten steel after the tapping from a converter to analyze S concentration thereof and determining acceptance/rejection of S and/or subsequent desulfurizing condition, wherein the S concentration is analyzed by a method using an ultraviolet fluorescence method.

The method of analyzing the S concentration in the molten steel desulfurization method according to the first aspect of the invention is preferable to comprise a high frequency induction heating step wherein the sample is combusted and oxidized under the high frequency induction heating in a pure oxygen atmosphere to convert S in molten steel into $SO_2$ and an analyzing step wherein $SO_2$-containing gas produced in the high frequency induction heating step is analyzed through an ultraviolet fluorescence method to quantify S concentration of the sample.

In the molten steel desulfurization method according to the first aspect of the invention, it is preferable that a target S concentration in the desulfurization is not more than 0.003 mass %.

The desulfurizing condition in the molten steel desulfurization method according to the first aspect of the invention is preferable to be at least one of an amount of a desulfurizer charged in the desulfurization and a treating time (molten steel stirring time or the like).

In the molten steel desulfurization method according to the first aspect of the invention, it is further preferable that when molten steel after the tapping from the converter is continuously subjected to a secondary refining, S concentration of a sample taken out from molten steel during the secondary refining is analyzed by using the above ultraviolet fluorescence method for determining the subsequent desulfurizing condition based on such S concentration.

Also, the first aspect of the invention is a method of manufacturing molten steel by using any one of the aforementioned molten steel desulfurization methods.

Furthermore, the inventors have made various studies on a method for rapidly and accurately analyzing S concentration of molten steel during the secondary refining for solving the above task. As a result, it has been found out that the above task can be solved by combusting and oxidizing a sample taken out from molten steel during the secondary refining under a high frequency induction heating in a pure oxygen atmosphere to convert all S included in the sample into $SO_2$ for a short time and analyzing such a concentration of $SO_2$ through an ultraviolet fluorescence method, and the second aspect of the invention has been accomplished.

That is, the second aspect of the invention is a method for secondarily refining molten steel tapped from a converter, wherein S concentration of a sample taken out from molten steel during the refining is analyzed by using an ultraviolet fluorescence method for determining subsequent desulfurizing condition based on an analytical value of the S concentration.

The method of analyzing the S concentration in the secondary refining method according to the second aspect of the invention is preferable to comprise a high frequency induction heating step wherein the sample is combusted and oxidized under the high frequency induction heating in a pure oxygen atmosphere to convert S in molten steel into $SO_2$ and an analyzing step wherein $SO_2$-containing gas produced in the high frequency induction heating step is analyzed through an ultraviolet fluorescence method to quantify S concentration of the sample.

In the secondary refining method according to the second aspect of the invention, it is preferable that a target S concentration in the desulfurization is not more than 0.003 mass %.

The desulfurizing condition in the secondary refining method according to the second aspect of the invention is preferable to be at least one of an amount of a desulfurizer charged in the desulfurization and a treating time (molten steel stirring time or the like).

Also, the second aspect of the invention is a method of manufacturing molten steel by using any one of the aforementioned molten steel desulfurization methods.

Effect of the Invention

According to the first aspect of the invention, the S concentration of molten steel after the tapping from the converter can be analyzed and grasped rapidly and accurately, so that not only the desulfurization of molten steel can be rationalized to improve the on-target ratio of S but also the step disturbance due to the failure of S concentration can be prevented and the increase of the production cost due to the excessive desulfurization can be suppressed, and hence the industrially successful effect is large. According to the second aspect of the invention, the S concentration in molten steel during the secondary refining can be analyzed and grasped rapidly and accurately, so that not only the desulfurization of molten steel can be rationalized to improve the on-target ratio of S but also the increase of the production cost due to the excessive desulfurization can be suppressed or the productivity can be improved by reducing the desulfurizing time or the step disturbance due to the failure of S concentration can be prevented, and hence the industrially successful effect is very large.

BRIEF DESCRIPTION OF DRAWINGS

FIG. 1 is a schematic view illustrating a constructive example of S analyzing apparatus used in the first aspect and second aspect of the invention.

FIG. 2 is a flow chart showing desulfurization refining of molten steel in an embodiment of the first aspect of the invention.

FIG. 3 is a view showing a flow of desulfurization using LF in the second aspect of the invention.

FIG. 4 is a graph showing a transition between a treating time and S concentration during desulfurization using LF in the second aspect of the invention.

FIG. 5 is a view showing a flow of desulfurization using RH vacuum degassing apparatus in the second aspect of the invention.

EMBODIMENTS FOR CARRYING OUT THE INVENTION

Molten steel after the completion of decarburization blowing in a converter is poured from a tapping port into a ladle by tilting the converter, at where an alloying iron, a deoxidizer and the like are added to molten steel in the ladle. Thereafter, a converter sample taken out from molten steel in the ladle is analyzed to determine operational conditions in subsequent secondary refining. For example, an amount of a desulfurizer initially charged in the secondary refining is calculated from S analytical value of the converter sample, target S concentration and molten steel amount. After the start of desulfurization refining, samples are taken out repeatedly on the way to monitor desulfurization state, and the desulfurizer is additionally charged, if necessary, and the desulfurization refining is completed when S concentration of molten steel reaches to a given target concentration. Thus, the S concentration in molten steel is properly analyzed in the steel-making step, and the analyzed results are reflected on the operative conditions.

However, if the accuracy of S analysis is poor, deficiency and excess of desulfurization becomes large to bring about the failure of S concentration or increase of the production cost due to the unnecessary addition of the desulfurizer. Table 1 shows an example that either converter sample or ladle sample is outside of S concentration in charging for a product having a standard value of S concentration of not more than 0.003 mass % (acceptance is less than 35 massppm). The charge No. 1 is an example that although S concentration of the converter sample is acceptable in the analysis by the infrared absorption method, S concentration of its ladle sample is rejected in the analysis by the spectrophotometric method and such a converter sample is again analyzed by the spectrophotometric method to reveal the failure of S concentration in the converter sample (at a time of tapping from the converter). On the other hand, the charge Nos. 2~4 are an example that since the converter samples are rejected in the analysis by the infrared absorption method, additional desulfurization is conducted in the secondary refining and as a result, these converter samples are accepted in the re-analysis by the spectrophotometric method and hence excessive desulfurization is carried out in the secondary refining.

TABLE 1

| Analysis Condition Charge of | Converter sample | | | | Ladle sample (spectrophotometric method) | |
|---|---|---|---|---|---|---|
| | Analysis at tapping (infrared absorption method) | | Re-analysis (spectrophotometric method) | | | |
| Tapped Steel | S concentration (massppm) | Judgment | S concentration (massppm) | Judgment | S concentration (massppm) | Judgment |
| 1 | 33.4 | ○ | 35.8 | X | 36.0 | X |
| 2 | 35.1 | X | 33.7 | ○ | 30.9 | ○ |
| 3 | 35.3 | X | 33.4 | ○ | 31.4 | ○ |
| 4 | 35.9 | X | 34.3 | ○ | 31.3 | ○ |

In view of such a situation, the inventors have considered that it is necessary to determine subsequent desulfurizing conditions by rapidly and accurately grasping S concentration in molten steel in the tapping from the converter together with acceptance/rejection judgment of S concentration and conducted examinations on a method for rapidly analyzing S in steel with a high accuracy (the first aspect of the invention). The inventors have also considered that it is necessary to determine operative conditions of secondary refining (desulfurizing conditions) by rapidly and accurately grasping S concentration of molten steel during the secondary refining and conducted examinations on a method for rapidly analyzing S in steel with a high accuracy (the second aspect of the invention).

Consequently, it has been found that the above problems can be solved by using an ultraviolet fluorescence method as the method for analyzing the S concentration, and as a result, the invention has been accomplished.

The method for analyzing S concentration with the ultraviolet fluorescence method in the first aspect and second aspect of the invention will be described below.

FIG. 1 shows a constructive example of an analyzing apparatus using the ultraviolet fluorescence method. The ultraviolet fluorescence analyzing apparatus 1 comprises a pure oxygen supply means 2, a high frequency induction heating furnace 3 for combusting and oxidizing a sample 5 taken out from molten steel in a pure oxygen atmosphere supplied from the pure oxygen supply means 2 to convert S included in the sample 5 into $SO_2$, a dust filter 4 for removing grit and dust (dust) from $SO_2$-containing gas produced by combustion of the sample 5, and an ultraviolet fluorescence analyzer 6 for analyzing $SO_2$-containing gas after the removal of the dust by ultraviolet fluorescence method to quantify S in the sample.

The pure oxygen supply means 2 comprises a pure oxygen supply source (not shown) having an oxygen concentration of not less than 99.5 vol %, a pure oxygen supply line 21, and a flow controller 22 disposed on the pure oxygen supply line 21 as a flow controlling means. As the flow controller may be used a well-known flow controller, but it is preferable to use a mass flow controller capable of controlling a mass flow of pure oxygen from a viewpoint of controlling the flow amount of the gas supplied.

In the inside of the high frequency induction heating furnace 3 are arranged a ceramic crucible 31 for dissolving and combusting the sample 5, and a coil 32 enclosing the ceramic crucible 31, wherein the coil 32 is connected to an alternating-current source (not shown). In the high frequency induction heating furnace 3, the sample 5 in the ceramic crucible 31 is rapidly heated and dissolved in the pure oxygen atmosphere supplied from the pure oxygen supply means 2 by applying an alternating current of, for example, 10~20 MHz to the coil 32, while S included in the sample 5 is reacted with oxygen or oxidized (combusted) to produce $SO_2$ (gas). In the combustion of the sample 5, it is preferable to use a combustion improver such as tin, tungsten or the like. Because, the sample 5 can be rapidly combusted by charging the sample 5 and the combustion improver into the ceramic crucible 31 and heating them, and hence the analysis of the S concentration can be conducted rapidly.

The dust filter 4 is disposed between the high frequency induction heating furnace 3 and the ultraviolet fluorescence analyzer 6 for removing dusts, which are generated from the sample 5 and the combustion improver, from the $SO_2$-containing gas generated in the high frequency induction heating furnace 3 to protect the ultraviolet fluorescence analyzer 6 arranged at subsequent stage. As the dust filter 4, it is preferable to use ones having an excellent air permeability made from a material not adsorbing $SO_2$ such as silica fiber or polytetrafluoroethylene.

In the ultraviolet fluorescence analyzer 6, an ultraviolet ray having, for example, a wavelength of 220 nm is irradiated to the $SO_2$-containing gas and then a fluorescence (wavelength of 330 nm) emitted from $SO_2$ in turning from an excited state to a ground state is measured for a certain time, and thereafter S amount included in the sample 5 is calculated from an integration value of fluorescence intensity measured with a previously prepared calibration curve. As the ultraviolet fluorescence analyzer 6 can be used a well-known ultraviolet fluorescence analyzer, particularly an ultraviolet fluorescence analyzer comprising an ultraviolet generating source, a fluorescent cell for irradiating an ultraviolet ray to $SO_2$-containing gas and a photomultiplier tube (PMT) measuring an excitation light.

Next, the method of quantitatively analyzing S concentration of the sample 5 taken from molten steel will be described with the use of the ultraviolet fluorescence analyzing apparatus 1.

At first, the sample 5 and the combustion improver are charged into the ceramic crucible 31. Then, pure oxygen is continuously supplied from the pure oxygen supply means 2 to the high frequency induction heating furnace 3, while an alternating current is applied to the coil 32 to combust (oxidize) the sample 5 in the pure oxygen atmosphere. After dusts included in $SO_2$-containing gas produced by combustion of the sample 5 is removed by the dust filter 4, S concentration included in the sample 5 is quantified by measuring $SO_2$ amount of the $SO_2$-containing gas with the ultraviolet fluorescence analyzer 6.

According to the ultraviolet fluorescence analyzing apparatus 1, the sample 5 can be combusted rapidly and sufficiently with the high frequency induction heating furnace 3 in the pure oxygen atmosphere. In the ultraviolet fluorescence analyzing apparatus 1, $SO_2$ amount produced by combustion of the sample 5 is measured by the ultraviolet fluorescence analyzer 6, so that it is substantially free of the influence of steam included in a gas to be measured or a temperature of such a gas as compared to the conventional infrared absorption method conducting the measurement with an infrared ray detector. Therefore, it is not required to use a dehumidifier, an adsorption/concentration column (trap) of $SO_2$ or the like, and the quantitative analysis of S can be conducted rapidly and accurately with a simple apparatus. In the ultraviolet fluorescence analyzing apparatus 1, it is not also required to use a reference gas (comparison gas) during the measurement as used in the conventional technique.

Also, oxygen absorbs fluorescence emitted in the turning of $SO_2$ from an excitation state to a ground state, or collide with the excited $SO_2$ molecule to cause quenching (extinction) phenomenon. To this end, it is known in the ultraviolet fluorescence method that the measuring accuracy of $SO_2$ concentration decreases when $SO_2$ amount in the gas to be measured is low or when a great amount of oxygen is contained in the gas to be measured. In the ultraviolet fluorescence analyzing apparatus 1 of the invention, however, all S in the sample 5 can be oxidized in a short time with the high frequency induction heating furnace 3 combusting the sample in the pure oxygen atmosphere. As a result, $SO_2$ concentration in the gas to be measured is high and the fluorescence intensity measured by the ultraviolet fluorescence analyzer 6 indicates a pointed sharp peak, so that $SO_2$ amount can be measured accurately.

Since oxygen has an action of quenching fluorescence of $SO_2$ as previously mentioned, even if gases of the same $SO_2$ concentration are measured in the ultraviolet fluorescence method, fluorescence of different intensity is detected depending upon the oxygen concentration included in the gas to be measured ($SO_2$-containing gas). Also, when the sample taken out from molten steel is combusted, oxygen bonds to hydrogen, carbon and the like included in the sample other than S, so that non-oxygen gas other than $SO_2$ gas is generated.

In order to eliminate the bad influence of oxygen in the ultraviolet fluorescence analyzing apparatus used in the invention, therefore, it is preferable to supply pure oxygen so that a difference between oxygen concentration in the pure oxygen supplied to the high frequency induction heating furnace and oxygen concentration in the $SO_2$-containing gas produced by combustion of the sample is not more than 10 vol %, concretely the oxygen concentration in the $SO_2$-containing gas produced by combustion of the sample is not less than 90 vol %. Because, when the sample is combusted, the oxygen concentration in the $SO_2$-containing gas is decreased by the formation of the non-oxygen gas as compared to the pure oxygen supplied to the high frequency induction heating furnace, but if the oxygen concentration in the $SO_2$-containing gas after the combustion is made to not less than 90 vol %, the change of fluorescence intensity measured due to the change of the oxygen concentration becomes small, so that $SO_2$ amount can be measured accurately.

Also, pure oxygen shortens a time until the $SO_2$-containing gas produced in the high frequency induction heating furnace 3 arrives at the ultraviolet fluorescence analyzer 6 and shortens a time required for the analysis. Further, it is desirable to ensure a flow amount exceeding a given amount in order to prevent the produced $SO_2$ from retaining in the apparatus. However, if the flow amount of pure oxygen is too large, $SO_2$ concentration in the $SO_2$-containing gas is decreased to lower the measuring accuracy or the frequency of clogging the dust filter 4 with dusts is increased, so that it is preferable to properly adjust the flow amount of pure oxygen in accordance with the size of the analyzing apparatus.

In the ultraviolet fluorescence method of the invention, the sample to be measured is combusted by high frequency induction heating in the pure oxygen atmosphere for a short time as mentioned above, so that S included in the sample can be oxidized into $SO_2$ rapidly and sufficiently. In the ultraviolet fluorescence method of the invention, the $SO_2$-containing gas produced by the combustion of the sample is also analyzed by an ultraviolet fluorescence method substantially free of background, so that S included in the sample can be analyzed in a higher accuracy.

According to the S analyzing method using the ultraviolet fluorescence method of the invention, therefore, S concentration included in the sample can be quantitatively analyzed rapidly in a high accuracy. When this method is applied to the sample taken out from molten steel, S concentration in molten steel can be quantitatively analyzed rapidly and accurately.

As a method of taking out a sample from molten steel for analyzing S concentration can be used a method disclosed for example, in JIS G1215-3(2010) or the like, but any methods may be used.

Table 2 shows results obtained by analyzing Japanese steel standard materials having S certified values of 9.4 massppm and 20 massppm in The Japan Iron and Steel Federation five times by an infrared absorption method defined in JIS G1215-4(2010) and an analysis method using the ultraviolet fluorescence method according to the invention, respectively. As to the infrared absorption method are carried out two methods, i.e. a method wherein the measurement is commonly conducted two times in a process to take an average value (common method) and a method wherein a sample is combusted to condense $SO_2$ in a condensing column (trap) and then released with a slight amount of helium gas for measurement in order to enhance an analyzing accuracy (condensation method).

TABLE 2

| | | Measuring sample | | | | | |
|---|---|---|---|---|---|---|---|
| | | JSS 653-14 (S certified value: 9.4 massppm) | | | JIS 244-9 (S certified value: 20 massppm) | | |
| | | Infrared absorption method | | | Infrared absorption method | | |
| Analyzing method | | common method | condensation method | Invention method | common method | condensation method | Invention method |
| Analytical value (massppm) | analysis 1 | 9.01 | 9.24 | 9.40 | 21.31 | 20.21 | 20.12 |
| | analysis 2 | 9.42 | 9.37 | 9.37 | 19.35 | 19.94 | 20.07 |
| | analysis 3 | 9.86 | 9.21 | 9.45 | 19.58 | 19.45 | 19.98 |
| | analysis 4 | 9.71 | 9.46 | 9.38 | 20.52 | 20.50 | 20.10 |
| | analysis 5 | 9.22 | 9.51 | 9.46 | 19.28 | 19.78 | 19.82 |
| Average value | | 9.44 | 9.36 | 9.42 | 20.01 | 19.98 | 20.02 |
| $\sigma_{n-1}$ | | 0.347 | 0.132 | 0.033 | 0.879 | 0.402 | 0.123 |

As seen from the results of Table 2, S concentration can be analyzed in a very high accuracy by using a method for analyzing S concentration according to the invention as compared with the conventional infrared absorption method (common method) and even the further use of the condensation method, and the difference of the accuracy is particularly remarkable in the extremely-low sulfur steel having a lower S concentration. Therefore, when the method for analyzing S concentration with the ultraviolet fluorescence method of the invention is applied to the analysis of S concentration in molten steel (especially analysis of S concentration in extremely low-sulfur steel), S concentration can be analyzed rapidly and accurately without conducting plural analyses, so that not only the acceptance/rejection judgment of S concentration in the desulfurization of molten steel can be conducted in a higher accuracy but also desulfurizing conditions in the secondary refining can be rationalized, and hence molten steel can be desulfurized without causing poor desulfurization or without bringing about the increase of the production cost due to excessive desulfurization.

Moreover, S concentration in molten steel during the secondary refining does not rise due to sulfur returning under usual operative conditions as long as special operation such as oxygen blowing or the like is not conducted. Therefore, the desulfurizer can be charged during the desulfurization so that S concentration of molten steel after the desulfurization is a value by about 1 massppm lower than the standard value (standard for acceptance/rejection judgment), so that the excessive charge of the desulfurizer can be suppressed to reduce the production cost.

Therefore, molten steel can be manufactured stable within the criterion of S concentration by refining with the desulfurization method according to the invention.

Table 3 shows the comparison of a time required in the analysis by a method for enhancing the analyzing accuracy of Japanese steel standard material having S certified value of 20 massppm in The Japan Iron and Steel Federation among the common method of taking the average value by conducting the measurement two times and the condensation method of measurement one times through the infrared absorption method and the method of conducting measurement one times with the ultraviolet fluorescence method of the invention. As seen from this table, when S concentration is analyzed by the method of the invention, the analyzing time per one chance can be shortened by about 1~2 minutes.

That is, according to the method of the invention using the ultraviolet fluorescence method, S concentration included in the sample can be quantitatively analyzed not only a high accuracy but also very rapidly. Therefore, when this method is applied to the sample taken out from molten steel, S concentration in molten steel can be quantitatively analyzed rapidly and accurately.

TABLE 3

| Method for analyzing S concentration | | Time required for measurement (seconds) | |
| --- | --- | --- | --- |
| Infrared absorption method (common method) | two measurements | 60 (measurement) × 2 times = 120 | +80 |
| Infrared absorption method (condensation method) | condensation | 60 (condensation) + 85 (measurement) = 150 | +110 |
| Invention method (ultraviolet fluorescence method) | one measurement | 40 (measurement) × 1 times = 40 | 0 |

In the first aspect of the invention, it is desirable to conduct the desulfurization refining of molten steel according to the flow chart shown, for example, in FIG. 2. Concretely, it will be described with reference to the following examples.

Then, the secondary refining method according to the second aspect of the invention will be described with the aforementioned S analyzing method.

At first, the case that molten steel after the tapping from the converter is desulfurized in the secondary refining with a ladle refining installation (LF) disclosed in Patent Documents 1~4. In the ladle refining installation (LF), the interior may be rendered into a non-oxidizing atmosphere by covering a ladle with a refractory lid, and further the lid is provided with electrodes embedded in a slag and heating molten steel by arc discharge, an injection lance for blowing auxiliary material such as CaO, Alumina-based desulfurizer, flux or the like into molten steel with an inert gas, and another lance or bottom tuyere for blowing an inert gas to stir molten steel.

FIG. 3(a) schematically shows a general treatment flow when desulfurization refining is carried out in the above LF, wherein given amounts of auxiliary materials such as desulfurizer, flux and the like are first charged into the LF based on analytical results of S concentration of a converter sample and so on and thereafter molten steel is agitated by starting an inert gas blowing to promote desulfurization reaction through "slag-metal reaction". After a given elapse time from the start of secondary refining, desulfurization state is grasped by taking out a sample from molten steel and analyzing S concentration thereof, and desulfurization is continued by additionally charging the auxiliary materials based on the analyzing results. After a further given elapse time, a sample is again taken out from molten steel to analyze S concentration, and acceptance/rejection judgment of S concentration is conducted based on the analyzed results. In case of the acceptance, the treatment is ended. In case of the rejection, the auxiliary materials are further additionally charged to continue the treatment for a given time, and then a sample is taken out from molten steel to confirm S concentration after the desulfurization.

FIG. 4 shows a transition between LF treating time and S concentration in molten steel when molten steel of three charges A~C is desulfurized to an extremely low-sulfur steel having a target S concentration of not more than 0.001 mass % (acceptance is not more than 14 massppm) with the conventional infrared absorption method as a method for analyzing S concentration in the secondary refining. In either charge, the first sample is taken out after 20 minutes from the start of the treatment, and the analyzed result of S concentration is revealed after 30 minutes. Based on this result, the auxiliary material such as desulfurizer or the like is additionally charged, and the second sample is taken out after 40 minutes, and the analyzed result of S concentration is revealed after 50 minutes. In the charge A, the S concentration is rejection after 50 minutes, so that the auxiliary material is again additionally charged and the LF treatment is ended after 60 minutes. In the charges B and C, the S concentration is acceptance, but the treatment is continued for 50 minutes until the analyzed result is revealed.

When the infrared absorption method of the conventional technique is applied as mentioned above, a time from the obtention of the sample to revelation of analyzed result of S concentration (sample transfer-pretreatment-analysis) is required to be a long time of about 10 minutes. Therefore, if it is intended to avoid insufficient desulfurization due to a large error of analyzing accuracy or to shorten the treating time, the desulfurizer is excessively charged before the revelation of the analyzed result on the sample as shown in FIG. 3(a). In this case, however, if the S concentration meets the standard from the analyzed result, the additional charging of the excessive auxiliary material and the prolongation of the treating time associated therewith become useless actions.

On the contrary, when the S analyzing method of the invention is applied to the secondary refining as shown in FIG. 3(b), a time required for one analysis can be shortened, and hence subsequent action can be hastened. Furthermore, when two analyses are carried out as shown in FIG. 3, the treating time can be further shortened. In addition to the shortening of the measuring time, since the S analyzing method of the invention is considerably excellent in the analyzing accuracy as compared with the conventional infrared absorption method, the excessive charge of the desulfurizer or the excessive prolongation of the treating time is not required, and the cost of the auxiliary material can be reduced or the excessive prolongation of the treating time can be prevented.

Table 4 shows a comparison in LF treating time and amount of auxiliary materials used when the conventional infrared absorption method shown in Table 3 (two measurements) and the ultraviolet fluorescence method of the invention shown in Table 3 are applied to secondary refining process wherein molten steel after the tapping from the converter is secondarily refined in LF to make a low-carbon aluminum killed steel having a target S concentration of not more than 0.001 mass % (standard on acceptance/rejection judgment: not more than 14 massppm). Moreover, the number of the treatments in each case is 30 charges.

TABLE 4

| Method for analyzing S concentration | | LF treatment | | |
|---|---|---|---|---|
| | | LF treating time (minutes) | Amount of lime used (kg/t) | Amount of calcium aluminate used (kg/t) |
| Conventional method | Infrared absorption method (JIS G1215-4) | 59 | 7.8 | 1.7 |
| Invention method | Ultraviolet fluorescence method | 55 | 7.3 | 1.5 |
| | Difference | −4 (−6.8%) | −0.5 (−6.4%) | −0.2 (−11.8%) |

As seen from Table 4, when the analyzing method using the ultraviolet fluorescence method of the invention is applied to the analysis of S concentration in the secondary refining of molten steel using LF, the time required for desulfurization refining can be shortened, and also the amount of the auxiliary materials such as desulfurizer, flux and the like can be largely reduced based on the improvement of the analyzing accuracy.

Next, the second aspect of the invention will be described with respect to a case that molten steel after the tapping from the converter is desulfurized in the secondary refining using RH vacuum degassing apparatus disclosed in Patent Documents 5~8. In the RH vacuum degassing apparatus, two dip tubes arranged in the bottom of a vacuum chamber are dipped in molten steel inside a ladle charged with a given amount of an auxiliary material (flux) based on the analytical results on S concentration and the like of a converter sample, at where molten steel is circulated by blowing an argon gas from one of the dip tubes to raise molten steel and discharging from the other dip tube, and the interior of the vacuum chamber is evacuated to remove gas ingredients in molten steel, while a desulfurizer such as pre-melt lime-alumina based flux or the like, or an alloy iron is charged from above of the vacuum chamber to conduct desulfurization or adjustment of alloying ingredients.

FIG. 5(a) schematically shows a general treatment flow when the conventional emission spectrometric method is used for analysis of S concentration when desulfurization is carried out in the secondary refining with the RH vacuum degassing apparatus. Even when the refining is carried out in the RH vacuum degassing apparatus, a sample is taken out from molten steel after a given elapse time from the start of the refining (reflux) and S concentration thereof is analyzed to grasp desulfurization state, and acceptance/rejection judgment of S concentration is conducted based on the analyzed result. In case of the acceptance, the treatment is ended, while in case of the rejection, the desulfurizer is further additionally charged and the treatment is continued for a given time and then ended. In either case, a sample is taken out form molten steel after the end of the treatment to confirm S concentration.

Moreover, the emission spectrometric analyzing apparatus is frequently disposed at the side of the RH vacuum degassing apparatus, but the preparation of an analyzing sample takes a certain time, so that a time from the obtention of the sample to revelation of the analyzed result (pretreatment-analysis) is about 10 minutes. If it is intended to avoid insufficient desulfurization due to a large error of analyzing accuracy or to shorten the treating time, the desulfurizer or the like is excessively charged before the revelation of the analyzed result on the sample likewise LF. Therefore, if the S concentration meets the standard from the analyzed result, the additional charging of the excessive auxiliary material and the prolongation of the treating time associated therewith become useless actions.

When the S analyzing method of the invention is applied to the secondary refining in the RH vacuum degassing apparatus, a time required for one analysis can be shortened, and hence subsequent action can be hastened and the treating time can be shortened as shown in FIG. 5(b). In addition to the shortening of the measuring time, since the S analyzing method of the invention is considerably excellent in the analyzing accuracy as compared with the conventional emission spectrometric method, the excessive charge of the desulfurizer or the excessive prolongation of the treating time is not required, and the cost of the auxiliary material can be reduced or the excessive prolongation of the treating time can be prevented.

Table 5 shows a comparison in RH treating time and amount of desulfurizer used when the conventional emission spectrometric method shown in FIG. 5(a) and the ultraviolet fluorescence method of the invention shown in FIG. 5(b) are applied to secondary refining process wherein molten steel after the tapping from the converter is secondarily refined in the RH vacuum degassing apparatus to make a low-carbon aluminum killed steel having a target S concentration of not more than 0.003 mass % (standard on acceptance/rejection judgment: not more than 35 massppm). Moreover, the number of the treatments in each case is 60 charges.

TABLE 5

| Method for analyzing S concentration | | RH treatment | |
|---|---|---|---|
| | | RH treating time (minutes) | Amount of desulfurizer used (kg/t) |
| Conventional method | Emission spectrometric method (JIS G1253) | 29 | 2.4 |
| Invention method | Ultraviolet fluorescence method | 27 | 2.1 |
| | Difference | −2 (−6.9%) | −0.3 (−12.5%) |

As seen from Table 5, when the analyzing method using the ultraviolet fluorescence method of the invention is applied to the analysis of S concentration in the secondary refining of molten steel using the RH vacuum degassing apparatus, the time required for desulfurization refining can be shortened, and also the amount of desulfurizer can be largely reduced based on the improvement of the analyzing accuracy.

Moreover, there is no damper in the simultaneous operation of the first and second aspects of the invention. For example, the analytical value of S concentration obtained by applying the ultraviolet fluorescence method of the invention to the sample taken out at the tapping from the converter (converter sample) is used as an indication to add the desulfurizer, and also S concentration is further analyzed by applying the ultraviolet fluorescence method of the invention to the sample taken out from molten steel during the secondary refining and subsequent desulfurizing conditions are determined based on the analyzed results, whereby the desulfurization can be carried out more efficiently in a higher accuracy. That is, the effects of the invention can be received at a time of taking out each sample by analyzing S concentration in molten steel with the ultraviolet fluorescence method of the invention applied to at least one of a sample taken out from molten steel after the tapping from the converter (converter sample) and a sample taken out from molten steel during the secondary refining and conducting determination of subsequent desulfurizing conditions (inclusive of determining presence or absence of desulfurization).

Example 1

There will be described an example of the first aspect of the invention wherein a method for analyzing S concentration with the ultraviolet fluorescence method of the invention is applied to a process of secondarily refining molten steel after the tapping from a converter by a method using a RH vacuum degassing apparatus (for example, a method disclosed in Patent Documents 7~8) to make a low-carbon aluminum killed steel having a target S concentration of not more than 0.002 mass % (standard on acceptance/rejection judgment: acceptance is less than 25 massppm).

In the RH vacuum degassing apparatus, as mentioned in the second aspect of the invention, two dip tubes arranged in the bottom of a vacuum chamber are dipped in molten steel at a state of charging a given amount of an auxiliary material (flux), at where molten steel is circulated by blowing an argon gas from one of the dip tubes to raise molten steel and discharging from the other dip tube, and the interior of the vacuum chamber is evacuated to remove gas ingredients in molten steel, while a desulfurizer such as pre-melt lime-alumina based flux or the like, or an alloy iron is charged from above of the vacuum chamber to conduct desulfurization or adjustment of alloying ingredients.

Invention Example

At first, hot metal having S concentration previously reduced to 10~20 massppm by a preliminary treatment of hot metal (measuring method: fluorescent X-ray method) is subjected to decarburization refining in a converter to obtain molten metal of about 250 tons, which is tapped into a ladle. In this case, a rod-shaped converter sample is taken out from molten steel in the ladle with a pin sampler, and then the rod-shaped sample is cut into a piece having a length of about 5 mm with a bolt clipper, which is weighed and placed in an analyzing apparatus of FIG. 1 using the ultraviolet fluorescence method of the invention to analyze S concentration. In this analysis, tungsten and tin are used as a combustion improver, and pure oxygen having an oxygen concentration of 99.99 vol % is used in the analysis and a flow amount of pure oxygen is 4 L/min and the analysis number is one.

Then, aluminum dross (metallic Al content: 30 mass %) is added to molten steel housed in the ladle to conduct reduction treatment of a slag to thereby adjust a total content of FeO and MnO in the slag to 2.8 mass %. Thereafter, the ladle is transferred to an RH vacuum degassing apparatus, at where molten steel having S concentration in the converter sample of less than 25 massppm is subjected to vacuum degassing treatment without desulfurization, while molten steel having the S analyzed value of not less than 25 massppm is subjected to vacuum degassing treatment (secondary refining) for desulfurization as mentioned later (20 charges in total).

Desulfurization in RH vacuum degassing apparatus: After the reflux of molten steel is started in the molten steel in the RH vacuum degassing apparatus, molten steel is deoxidized by charging Al into the vacuum degassing apparatus and then a pressure in the vacuum degassing apparatus is made to 2.6~3.9 kPa (20~30 torr) to further reflux molten steel. During the reflux of molten steel, a pre-melt flux for desulfurization comprising CaO: 57 mass %, $Al_2O_3$: 42 mass % and $SiO_2$: 1 mass % (particle size: 10~150 μm) is projected onto a surface of molten steel in the vacuum degassing apparatus through a top-blowing lance inserted from above the vacuum degassing apparatus with Ar gas as a carrier gas. Moreover, the amount of the pre-melt flux for desulfurization projected for desulfurization treatment per 1 ton of molten steel is a weight (kg) obtained by multiplying 0.18 to a difference between S analyzed result of the converter sample and (upper limit of target S concentration−1 massppm) (=24 massppm). Moreover, when the multiplier factor is 0.18, even if the charging amount is determined based on the analyzed value of S concentration in the converter sample by the conventional method (see the following Comparative Example), it has been confirmed by the inventors' experiment that S concentration after the desulfurization arrives at less than the target upper limit.

Thereafter, a sample is taken out from molten steel after the completion of secondary refining in the RH vacuum degassing apparatus with or without desulfurization to analyze S concentration by a spectrophotometric method having a high analyzing accuracy and defined in JIS G1215-3.

Comparative Example

Except that S concentration of the converter sample taken out at the tapping from the converter is analyzed by an infrared absorption method of JIS G1215-4 (common method), 20 charges of steel tapped from the converter are subjected to the RH vacuum degassing treatment likewise the aforementioned Invention Example, and S concentration after the treatment is analyzed by the same spectrophotometric method as in Invention Example.

In Table 6 is shown a comparison between average value and standard deviation $\sigma_{n-1}$ of S concentration in the results analyzed by the spectrophotometric method on 20 charges of molten steel after the completion of RH degassing treatment in the above Invention Example and Comparative Example, respectively. As seen from these results, there is no great difference in the average value of S concentration between Invention Example and Comparative Example and these values satisfy standard value of acceptance/rejection judgment of less than 25 massppm, while the standard deviation $\sigma_{n-1}$ in Invention Example is not more than ½ of that in Comparative Example or the desulfurization method of the invention is right in the amount of the desulfurizer charged as compared with Comparative Example.

TABLE 6

| Analyzing method of converter sample | | Analyzed value of sample after RH treatment (spectrophotometric method) | |
|---|---|---|---|
| | | Average value (massppm) | Standard deviation $\sigma_{n-1}$ (massppm) |
| Invention Example | Invention method | 22.1 | 0.6 |
| Comparative Example | Infrared absorption method | 22.6 | 1.5 |

Also, Table 7 shows a comparison between S analyzed value of converter sample and S analyzed value (spectrophotometric method) of the sample after RH treatment on all of charges not subjected to desulfurization in RH vacuum degassing apparatus among 20 charges of each of Invention Example and Comparative Example because the S analyzed value of the converter sample is less than 25 massppm (acceptance of S concentration). As seen from Table 7, there is not great difference in the number of charges having the acceptance of S concentration of the converter sample between Invention Example and Comparative Example, but the failure of S concentration after RH treatment is caused in two charges of Comparative Example. This is due to the fact that the S concentration of the converter sample intrinsically being rejection was judged to be acceptance because the accuracy of S concentration of the converter sample is poor.

TABLE 7

|  |  | Converter sample | | Sample after RH treatment | | |
|---|---|---|---|---|---|---|
|  | Number of charges | Analyzing method | Analyzed value (massppm) | Analyzing method | Analyzed value (massppm) | Acceptance/rejection judgment |
| Invention Example | 1 | Invention method | 24.3 | Spectrophotometric method | 24.2 | ○ |
|  | 2 | Invention method | 23.9 | Spectrophotometric method | 23.7 | ○ |
|  | 3 | Invention method | 24.2 | Spectrophotometric method | 24.2 | ○ |
|  | 4 | Invention method | 23.7 | Spectrophotometric method | 23.8 | ○ |
|  | 5 | Invention method | 24.0 | Spectrophotometric method | 24.2 | ○ |
|  | 6 | Invention method | 23.6 | Spectrophotometric method | 23.5 | ○ |
| Comparative Example | 1 | Infrared absorption method | 24.0 | Spectrophotometric method | 25.5 | x |
|  | 2 | Infrared absorption method | 23.7 | Spectrophotometric method | 23.0 | ○ |
|  | 3 | Infrared absorption method | 22.9 | Spectrophotometric method | 24.2 | ○ |
|  | 4 | Infrared absorption method | 23.9 | Spectrophotometric method | 25.2 | x |
|  | 5 | Infrared absorption method | 24.2 | Spectrophotometric method | 23.1 | ○ |

Example 2

An example relating to simultaneous operation of the first aspect and second aspect of the invention will be described by further applying the ultraviolet fluorescence method of the invention to the analysis of S concentration when subsequent desulfurizing conditions are determined based on S concentration of a sample taken out from molten steel at a stage on the way of secondary refining in a process of manufacturing a low-carbon aluminum killed steel with a target S concentration of not more than 0.002 mass % (standard on acceptance/rejection judgment: acceptance is less than 25 massppm) likewise Example 1.

At first, hot metal having S concentration previously reduced to 10~20 massppm by a preliminary treatment of hot metal (measuring method: fluorescent X-ray method) is subjected to decarburization refining in a converter to obtain molten metal of about 250 tons, which is tapped into a ladle. In this case, a rod-shaped converter sample is taken out from molten steel in the ladle with a pin sampler, and then the rod-shaped sample is cut into a piece having a length of about 5 mm with a bolt clipper, which is weighed and placed in an analyzing apparatus of FIG. 1 using the ultraviolet fluorescence method of the invention to analyze S concentration. In this analysis, tungsten and tin are used as a combustion improver, and pure oxygen having an oxygen concentration of 99.99 vol % is used in the analysis and a flow amount of pure oxygen is 4 L/min and the analysis number is one.

Then, aluminum dross (metallic Al content: 30 mass %) is added to molten steel housed in the ladle to conduct reduction treatment of a slag to thereby adjust a total content of FeO and MnO in the slag to 2.8 mass %. Thereafter, the ladle is transferred to an RH vacuum degassing apparatus, at where molten steel having S concentration in the converter sample of not less than 25 massppm as measured by the ultraviolet fluorescence method of the invention is subjected to vacuum degassing treatment (secondary refining) for desulfurization by the following two methods on 20 charges, respectively.

Invention Example 1

After the reflux of molten steel is started in the molten steel in the RH vacuum degassing apparatus, molten steel is deoxidized by charging Al into the vacuum degassing apparatus and then a pressure in the vacuum degassing apparatus is made to 2.6~3.9 kPa (20~30 torr) to further reflux molten steel. During the reflux of molten steel, a pre-melt flux for desulfurization comprising CaO: 57 mass %, $Al_2O_3$: 42 mass % and $SiO_2$: 1 mass % (particle size: 10~150 μm) is projected onto a surface of molten steel in the vacuum degassing apparatus through a top-blowing lance inserted from above the vacuum degassing apparatus with Ar gas as a carrier gas. Moreover, the amount of the pre-melt flux for desulfurization projected for desulfurization treatment per 1 ton of molten steel is a weight (kg) obtained by multiplying 0.17 to a difference between S analyzed result of the converter sample and (upper limit of target S concentration−1 massppm) (=24 massppm). The reason why the multiplier factor is 0.17 lower than 0.18 of Example 1 is to suppress excessive charging of the pre-melt flux for desulfurization as far as possible. As mentioned in Example 1, when the multiplier factor is 0.18, S concentration after the desulfurization arrives at a value less than the target upper limit in all of charges. On the contrary, when the multiplier factor is 0.17, it has been confirmed by the inventors' experiments that S concentration after the desulfurization may not arrive at a value less than the target upper limit in a certain charge.

After a lapse of a given time from the start of reflux, a sample is taken out from molten steel to analyze S concentration in molten steel by the ultraviolet fluorescence method of the invention (analyze during the secondary refining). As a result, when S concentration does not arrive at less than 25 massppm, the pre-melt flux for desulfurization is additionally charged at a weight (kg) obtained by multiplying 0.18 to a difference between S analyzed result of the converter sample (analyzing during the second refining) and (upper limit of target S concentration−1 massppm) (=24 massppm) per 1 ton of molten steel.

Thereafter, a sample is taken out from molten steel after the completion of secondary refining in the RH vacuum degassing apparatus (desulfurization) to analyze S concentration by a spectrophotometric method having a high analyzing accuracy and defined in JIS G1215-3.

Invention Example 2

For the purpose of comparing with Invention Example 1, the secondary refining (desulfurization) is carried out as follows. A different point to Invention Example 1 lies in that the amount of the pre-melt flux for desulfurization projected for desulfurization treatment during the RH vacuum degassing treatment is a weight (kg) obtained by multiplying 0.18 to a difference between S analyzed result of the converter sample and (upper limit of target S concentration−1 massppm) (=24 massppm) per 1 ton of molten steel and S concentration in molten steel is not measured during the RH vacuum degassing treatment and hence the additional charging of the desulfurizer is not conducted on the way of the secondary refining. Molten steel tapped from the converter is subjected to RH vacuum degassing treatment in the same manner as in Invention Example 1 other than the above, and S concentration in molten steel after the secondary refining is analyzed by the spectrophotometric method likewise Invention Example 1.

Table 8 shows results of S concentration in molten steel analyzed by the spectrophotometric method after 20 charges of each of Invention Example 1 and Invention Example 2 are subjected to secondary refining with the RH vacuum degassing apparatus. As seen from these results, the accuracy of the desulfurization is further improved in Invention Example 1 that after the desulfurizer is charged based on S analyzed value obtained by applying the ultraviolet fluorescence method of the invention to the converter sample as an indication, the analyzed result of S concentration obtained by applying the ultraviolet fluorescence method of the invention to a sample of molten steel during the secondary refining (RH degassing treatment) is reflected onto subsequent desulfurizing conditions as compared with Invention Example 2 that the analysis of S concentration during the secondary refining and the additional charging of the desulfurizer are not carried out.

TABLE 8

| Presence or absence of reflection of result analyzed by ultraviolet fluorescence method during secondary refining (RH degassing treatment) on desulfurizing conditions | Sample after RH treatment | |
|---|---|---|
| | average value (massppm) | standard deviation $\sigma_{n-1}$ (massppm) |
| Invention Example 1 | presence | 23.1 | 0.5 |
| Invention Example 2 | absence | 22.3 | 0.7 |

INDUSTRIAL APPLICABILITY

Although the above explanation describes the invention by way of example of the analysis of S concentration in the desulfurization refining of molten steel (first aspect of the invention) or the secondary refining of molten steel after the tapping from the converter (second aspect of the invention), the invention can be applied, for example, to analysis of S concentration in another metal, which is hardly combusted, without limiting to such a field.

DESCRIPTION OF REFERENCE SYMBOLS

1: ultraviolet fluorescence analyzing apparatus
2: pure oxygen supply means
21: pure oxygen supply line
22: flow controller
3: high frequency induction heating furnace
31: ceramic crucible
32: coil
4: dust filter
5: sample
6: ultraviolet fluorescence analyzer

The invention claimed is:
1. A method for desulfurizing molten steel, the method comprising:
taking out a sample from molten steel after tapping from a converter;
analyzing S concentration of the sample using an ultraviolet fluorescence method;
determining at least one of (i) acceptance or rejection of S and (ii) a subsequent desulfurizing condition,
wherein the analyzing the S concentration of the sample using the ultraviolet fluorescence method comprises (1) a high frequency induction heating step wherein the sample is combusted and oxidized under the high frequency induction heating in an oxygen atmosphere supplied with a gas having an oxygen concentration of 99.5 vol % or more to convert S in molten steel into $SO_2$, and (2) an analyzing step in which $SO_2$-containing gas produced in the high frequency induction heating step is analyzed to quantify S concentration of the sample using the ultraviolet fluorescence method after removing dust from $SO_2$-containing gas produced by combustion of the sample,
a difference between the oxygen concentration in the gas supplied to the high frequency induction heating furnace and a free oxygen concentration in the $SO_2$-containing gas produced by combustion of the sample is not more than 10 vol %, and
combusting the sample includes adding a combustion enhancer selected from the group consisting of Sn and W.

2. The method for desulfurizing molten steel according to claim 1, wherein a target S concentration in the desulfurization is not more than 0.003 mass %.

3. The method for desulfurizing molten steel according to claim 1, wherein the desulfurizing condition is at least one of an amount of a desulfurizer added in the desulfurization and a treating time.

4. The method for desulfurizing molten steel according to claim 1, wherein when molten steel after the tapping from the converter is continuously subjected to a secondary refining, S concentration of a sample taken out from molten steel during the secondary refining is analyzed to determine the subsequent desulfurizing condition based on the S concentration.

5. The method for desulfurizing molten steel according to claim 1, further comprising suppressing excessive charge of a desulfurizer during desulfurizing by charging the desulfurizer so that the S concentration of the molten steel after desulfurization is lower than a predetermined value.

6. The method for desulfurizing molten steel according to claim 1, wherein removing the dust includes filtering the dust with a dust filter and controlling a flow amount of the gas having an oxygen concentration of 99.5 vol % to reduce clogging of the dust filter.

7. The method for desulfurizing molten steel according to claim 1, wherein quantifying S concentration of the sample includes measuring a fluorescence intensity of $SO_2$ in the $SO_2$-containing gas and comparing the measured intensity to a calibration curve to determine the S concentration of the sample before combustion.

8. A method of manufacturing molten steel by using a desulfurization method as claimed in claim 1.

* * * * *